(12) United States Patent
Hijlkema (10) Patent No.: US 11,376,375 B2
(45) Date of Patent: Jul. 5, 2022

(54) AEROSOL GENERATOR

(71) Applicant: KONINKLIJKE PHILIPS N.V., Eindhoven (NL)

(72) Inventor: Markus Hijlkema, Chichester (NL)

(73) Assignee: Koninklijke Philips N.V., Eindhoven (NL)

( * ) Notice: Subject to any disclaimer, the term of this patent is extended or adjusted under 35 U.S.C. 154(b) by 258 days.

(21) Appl. No.: 16/076,341

(22) PCT Filed: Jan. 25, 2017

(86) PCT No.: PCT/EP2017/051453
§ 371 (c)(1),
(2) Date: Aug. 8, 2018

(87) PCT Pub. No.: WO2017/137252
PCT Pub. Date: Aug. 17, 2017

(65) Prior Publication Data
US 2019/0038851 A1 Feb. 7, 2019

(30) Foreign Application Priority Data
Feb. 8, 2016 (EP) .................................... 16154653

(51) Int. Cl.
*B05B 17/06* (2006.01)
*A61M 11/00* (2006.01)
(Continued)

(52) U.S. Cl.
CPC ...... *A61M 11/005* (2013.01); *A61M 15/0085* (2013.01); *B05B 17/0638* (2013.01); *B05B 17/0653* (2013.01); *B05B 17/0646* (2013.01)

(58) Field of Classification Search
CPC ............. A61M 11/005; A61M 15/0085; B05B 17/0638; B05B 17/0653; B05B 17/0646
See application file for complete search history.

(56) References Cited

U.S. PATENT DOCUMENTS 709,848 A 9/1902 Creveling
4,850,534 A 7/1989 Takahashi
(Continued)

FOREIGN PATENT DOCUMENTS

DE 102307674 B 8/2014
DE 202015102538 U1 9/2015
(Continued)

*Primary Examiner* — Qingzhang Zhou
(74) *Attorney, Agent, or Firm* — Daniel H. Brean (57) ABSTRACT

Nebulizers are used to deliver a medicine to a patient's lungs in the form of an airstream, with fluid comprising the medicine entrained in the airstream. To enable the fluid to be entrained in the airstream, a nebulizer contains an aerosol generator typically comprising a vibratory element (28) with a piezoelectric actuator. There is a need to frequently sterilize the nebulizer. This involves dipping the nebulizer in boiling water for a significant time. It has been found that repeated sterilization cycles can force water through gaps in the vibratory element, and its encapsulation (26), and damage the piezo element. The present invention proposes to more effectively seal the piezo of the vibratory element (28) from the effects of water ingress. In particular, it is proposed to create, at an interface of the vibratory element (28) and the encapsulating element (26), a discontinuity which provides a barrier geometry. Through capillary forces, the progress of water towards the piezoelectric element (12) comprised in the vibratory element (28) is arrested, and the lifetime of the aerosol generator is improved.

12 Claims, 5 Drawing Sheets

(51) Int. Cl.
    *A61M 15/00*     (2006.01)
    *B05B 17/00*     (2006.01)

(56) References Cited

U.S. PATENT DOCUMENTS

| | | | |
|---|---|---|---|
| 6,014,970 A | 1/2000 | Ivri | |
| 6,702,277 B1 * | 3/2004 | Gaffal | B65H 29/40 |
| | | | 271/108 |
| 8,480,010 B2 | 7/2013 | Ishigami | |
| 8,578,931 B2 | 11/2013 | Ivri | |
| 8,870,090 B2 | 10/2014 | Feriani | |
| 9,108,211 B2 | 8/2015 | Ivri | |
| 2005/0178847 A1 * | 8/2005 | Power | A61M 11/005 |
| | | | 239/4 |
| 2006/0226253 A1 | 10/2006 | Wang | |
| 2010/0319685 A1 * | 12/2010 | Yu | B05B 17/0646 |
| | | | 128/200.16 |
| 2012/0012665 A1 | 1/2012 | Ivri | |
| 2014/0346245 A1 | 11/2014 | Van Der Sluis | |
| 2015/0060574 A1 * | 3/2015 | Kromer | F02M 61/168 |
| | | | 239/584 |
| 2016/0310981 A1 * | 10/2016 | Von Hollen | A61M 16/0054 |

FOREIGN PATENT DOCUMENTS

| | | | |
|---|---|---|---|
| EP | 1977778 A1 | 10/2008 | |
| EP | 2886185 A1 | 6/2015 | |
| JP | 5913264 | * | 7/1984 |
| JP | 3885744 B2 | 9/2004 | |
| JP | 2004257834 A | 9/2004 | |
| JP | 2006084565 A | 3/2006 | |
| WO | WO2008005030 A1 | 1/2008 | |
| WO | WO2015091564 A1 | 6/2015 | |

\* cited by examiner

AEROSOL GENERATOR

CROSS-REFERENCE TO RELATED APPLICATIONS

This patent application claims the priority benefit under 35 U.S.C. § 371 of international patent application no. PCT/EP2017/051453, filed Jan. 25, 2017, which claims the benefit of European Patent Application No. 16154653.6, filed on Feb. 8, 2016, the contents of which are herein incorporated by reference.

FIELD OF THE INVENTION

Aspects of the present invention relate to an aerosol generator for generating liquid droplets by nebulization, to a nebulizer, and to a method of manufacturing an aerosol generator.

BACKGROUND OF THE INVENTION

Aerosol generators for generating liquid droplets are used in various industries. An exemplary use is in nebulizers, to deliver pharmaceuticals in a droplet form, for inhalation by a patient. Maintaining good hygiene is one design consideration when designing nebulizer parts. Typically, a patient spends a considerable amount of time cleaning, and disinfecting a nebulizer. A typical disinfection procedure involves boiling the nebulizer for about ten minutes. A typical nebulizer needs to withstand a large number of boiling treatments.

Figure 1:
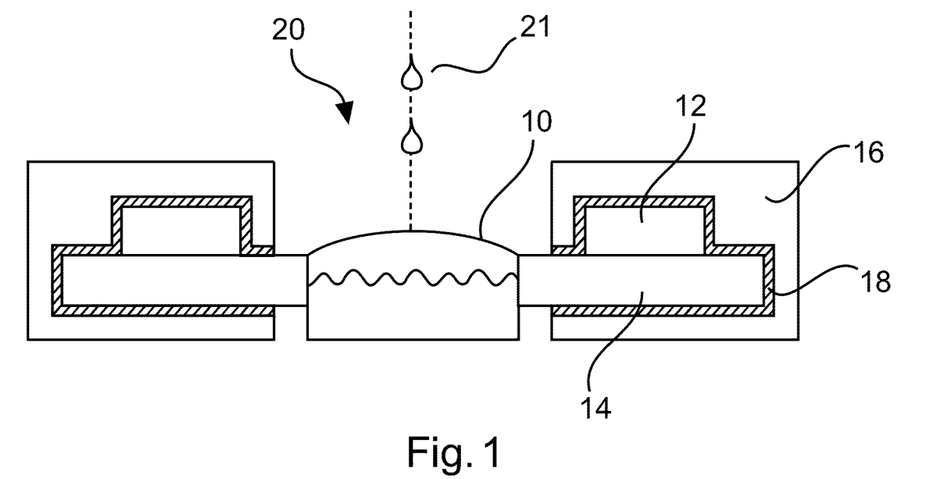
FIG. 1 shows a side-view of an aerosol generator as known in the prior art.

A general type of nebulizer is the vibrating mesh nebulizer 20. FIG. 1 shows a schematic diagram of a typical vibrating mesh nebulizer. A vibratory element comprising a piezoelectric element 12 (typically ring-shaped) atop a metal washer 14 (also typically ring-shaped) supports a mesh 10. A liquid reservoir 23 is provided underneath the mesh 10. The mesh may be brought into vibration by the action of the piezoelectric element 12 through the metal washer 14. A drop of liquid 21 is introduced (for example, by gravity) when the mesh 10 is vibrating, and an aerosol mist is produced. Residue is collected by the open top of the liquid reservoir 23. If the vibratory element is located in proximity to an air stream, the aerosol so produced will be entrained in the airstream. Typically, the vibratory element is encapsulated in an encapsulation element 16 (typically an overmoulding), and a protective encapsulation 18 may be provided.

A typical piezoelectric element 12 is made out of ceramic. If water molecules penetrate the ceramic, the piezoelectric element 12 will typically lose functionality. The encapsulation element 16, and the encapsulation 18 provide an imperfect seal, and water ingress into the piezoelectric element 12 in the presence of repeated, harsh boiling procedures may still present a problem.

WO 2015/091564 discusses a water-resistant nebulizer of the general type discussed above. Such nebulizers of this general type may, however, be further improved.

SUMMARY OF THE INVENTION

It would be advantageous to have an improved technique for sealing the vibratory element of an aerosol generator against water ingress.

Towards this end, a first aspect of the invention provides an aerosol generator for generating liquid droplets by nebulization, comprising:

an aperture member comprising a plurality of apertures to provide the liquid droplets;
a vibratory element arranged to generate a vibration of the aperture member; and
an encapsulation element arranged to encapsulate a portion of the vibratory element.

An interface region is provided between the vibratory element and the encapsulation element, wherein the interface region comprises a sealing portion comprising a liquid resisting seal, provided as a first discontinuity formed on a face of the vibratory element and/or the encapsulation element.

Therefore, an aerosol generator is provided with improved resistance to fluid ingress. This is because, traditionally, over moulded elastomers in contact with metal aerosol generator parts do not usually bond with the metal with chemical bonds, but only via a mechanical "locking" to granules of metal. Thus, there is a gap between the metal and the elastomer that enables fluid creepage.

According to an aerosol generator meeting the definition of the aerosol generator the first aspect, the first discontinuity formed on the face of the vibratory element acts as a barrier geometry, and functions to arrest the progress of the meniscus of an advancing fluid. In this way, the advancing fluid is stopped before it makes contact with the vibratory element. The first discontinuity causes an advancing liquid contact line to experience increased surface forces caused by the increase in surface area of the liquid contact line at the discontinuity.

In addition, the aerosol generator is actively vibrated by a vibratory element. The interface between the metal part and an over moulded elastomer causes stress at the interface, during vibration. This can cause the over moulded component to peel away from the metal as a result of the vibration, creating capillary spaces that can fill with fluid.

According to an aerosol generator meeting the definition of the aerosol generator the first aspect, the discontinuity also functions to increase the "lock-in" effect in the adhesion to the parts of the aerosol generator (for example, made of metal).

According to an embodiment of the first aspect, an aerosol generator is provided which further comprises an adhesive layer provided in the interface region.

According to this embodiment, the adhesive layer is also provided with discontinuities which present a liquid barrier to an advancing fluid.

According to an embodiment of the first aspect, an aerosol generator according to the first aspect is provided, wherein the vibratory element further comprises a piezo-electric element arranged in mechanical contact with an aperture member support structure, the aperture member support structure is configured to support the aperture member; and wherein the interface region is provided on a portion of the aperture member support structure.

According to this embodiment, a piezo-electric element may be protected from fluid ingress when attached to an aperture member support structure.

According to an embodiment of the first aspect, an aerosol generator according to the first aspect is provided, wherein the vibratory element has a first side and a second side, and the sealing portion comprises a first sealing portion and a second sealing portion disposed on the first and the second sides of the vibratory element, respectively.

According to this embodiment, fluid ingress may be prevented from affecting the operation of the vibratory element from several different directions.

According to an embodiment of the first aspect, an aerosol generator according to the first aspect is provided, wherein the first discontinuity has a depth in the range of 10 to 50 microns.

According to this embodiment, a preferred range of discontinuity depths having good fluid blocking performance is provided.

According to an embodiment of the first aspect, an aerosol generator according to the first aspect is provided, wherein the first discontinuity is provided as a groove, or a plurality of grooves.

According to this embodiment, the first discontinuity has at least two parallel edges, enabling improved fluid blocking performance.

According to an embodiment of the first aspect, an aerosol generator according to the first aspect is provided, wherein the groove, or grooves of the plurality of grooves, have an aspect ratio of 1.

According to this embodiment, the first discontinuity has proportions which make manufacturing of a fluid seal more practical.

According to an embodiment of the first aspect, an aerosol generator is provided wherein the plurality of grooves is disposed on first and second opposite sides of the vibratory element, and the grooves of the first opposite side are offset in relation to the grooves of the second opposite side.

According to this embodiment, a fluid seal having improved fluid resistance is provided.

According to an embodiment of the first aspect, an aerosol generator is provided wherein the encapsulation element further comprises a second discontinuity configured to form a complementary interlock structure with the first discontinuity of the vibratory element at the sealing portion.

According to this embodiment, a fluid seal preventing fluid ingress between an adhesive layer and the encapsulation element is provided, because the encapsulation element itself has discontinuities which cause a resistance to an advancing fluid by the mechanism of capillary action.

According to a second aspect of the invention, there is provided a nebulizer, comprising:
an aerosol generator according to the first aspect, or one of the embodiments of the first aspect.

Therefore, a more reliable nebulizer can be provided. An aerosol generator as described above will have a much lower risk of failure owing to the improved sealing properties of the vibratory element and encapsulation element.

According to a third aspect of the invention, there is provided a method of manufacturing an aerosol generator. The method comprises the steps of:
a) providing (60) a vibratory element arranged, in use of the component, to generate a vibration of an aperture member;
b) forming (62) a first discontinuity in a face of the vibratory element:
c) providing (64) an encapsulation element arranged to contact and encapsulate a portion of the vibratory element, to form an interface region incorporating a sealing portion with a liquid resisting seal provided by the first discontinuity.

Therefore, an aerosol element with more effective fluid resistance between the vibratory element and the encapsulation element can be manufactured, owing to the capillary action of the discontinuity against fluid droplets.

According to an embodiment of the third aspect, the method of manufacturing, further comprises:
b1) providing an adhesive on the interface region of a face of a vibratory element.

According to an embodiment of the third aspect, the method of manufacturing, further comprises:
b2) providing on a face of the encapsulation element a complementary second discontinuity arranged to interlock with the first discontinuity of the vibratory element at the sealing portion.

According to this embodiment, a fluid seal preventing fluid ingress between an adhesive layer and the encapsulation element is provided, because the encapsulation element itself has discontinuities which cause a resistance to an advancing fluid by the mechanism of capillary action.

According to an embodiment of the third aspect, the method of manufacturing, further comprises forming the first and/or second discontinuities on the respective vibratory element or encapsulation element using a laser engraving technique.

Accordingly, a discontinuity may be provided on the vibratory element, and/or the encapsulation element, in a simple way. Additionally, a laser engraving technique provides additional roughness in the area of the discontinuity, enhancing the "lock-in" effect of an interference fit, or of the effect of an adhesive.

In the following description, it is to be understood that the term "liquid droplets" includes liquid droplets having diameters in a range which makes them suitable for oral inhalation by a patient. Preferably, the droplets are provided in the order of microns.

In the following description, it is to be understood that the term "aperture member" includes a mesh which may be brought into vibratory action by a vibratory element. The mesh has holes which are suitable for producing liquid droplets on the order of microns, for example. As the aperture member vibrates against a droplet from a gravity feeding arrangement, or against a liquid surface, small droplets are created.

Therefore, it can be seen as a basic idea of the invention to add a barrier geometry to an aerosol generator. The barrier geometry prevents fluid ingress, which can damage piezoelectric components. The barrier geometry exploits the capillary effect present when a fluid droplet experiences a discontinuity.

These, and other aspects of the invention, will become apparent from, and are elucidated with reference to, the embodiments described hereinafter.

DETAILED DESCRIPTION OF EMBODIMENTS

As noted above, FIG. 1 shows a side view of a known configuration of a vibrating mesh aerosol generator. An aperture member 10, such as a mesh, is vibrated by a vibratory element, which in FIG. 1 is a piezoelectric element 12 which may, for example, be annular. The aperture member 10 is vibrated against the surface of a liquid, or has liquid droplets dropped onto it whilst the mesh vibrates, and an aerosol mist comprising fluid droplets is generated. The aerosol mist can be entrained in an airflow, enabling the delivery of pharmaceuticals to the lungs of a patient. The typical construction, discussed above, involves the piezoelectric element 12 being supported on a washer 14. The washer is usually metal. The piezoelectric element 12 and the washer 14 are embedded in an encapsulation element 16, typically with an adhesive layer 18 (such as an epoxy adhesive) between the washer 14, piezoelectric element 12, and the encapsulation element 16. The epoxy adhesive is intended to act as a first fluid barrier, and as a primer layer for a second barrier, which is the encapsulation element 16. As will be discussed below, it is, alternatively, possible to embed the piezoelectric element 12 and the washer 14, or analogous components, in the encapsulation element 16 without an adhesive layer 18. In this case, the surface of the encapsulation element 16 may optionally be activated using a solvent primer.

As discussed above, the encapsulation element 16 is typically intended to isolate the vibrations of the piezoelectric element 12 and washer 14, and to provide a mounting. In addition, sterilization of aerosol-generating elements is typically performed by holding the active end of the nebulizer, including the aerosol-generating element, in boiling water. Thus, the encapsulation element 16 and the adhesive layer 18 are also intended to provide a seal which is fluid-tight to a limited extent.

Experience has shown that water ingress into the piezoelectric element 12 is still a major failure mode of the prior-art aerosol generators discussed above. It takes considerable effort to make the encapsulation element 16 watertight. Aerosol-generators which fail frequently, thus require a more frequent replacement of the aerosol-generating element, or possibly replacement of the entire nebulizer unit, if the aerosol generating element is integrated, and not removable.

The water ingress occurs at the boundary of the washer 14, adhesive layer 18, and boundary of the encapsulation element 16.

Figure 2:
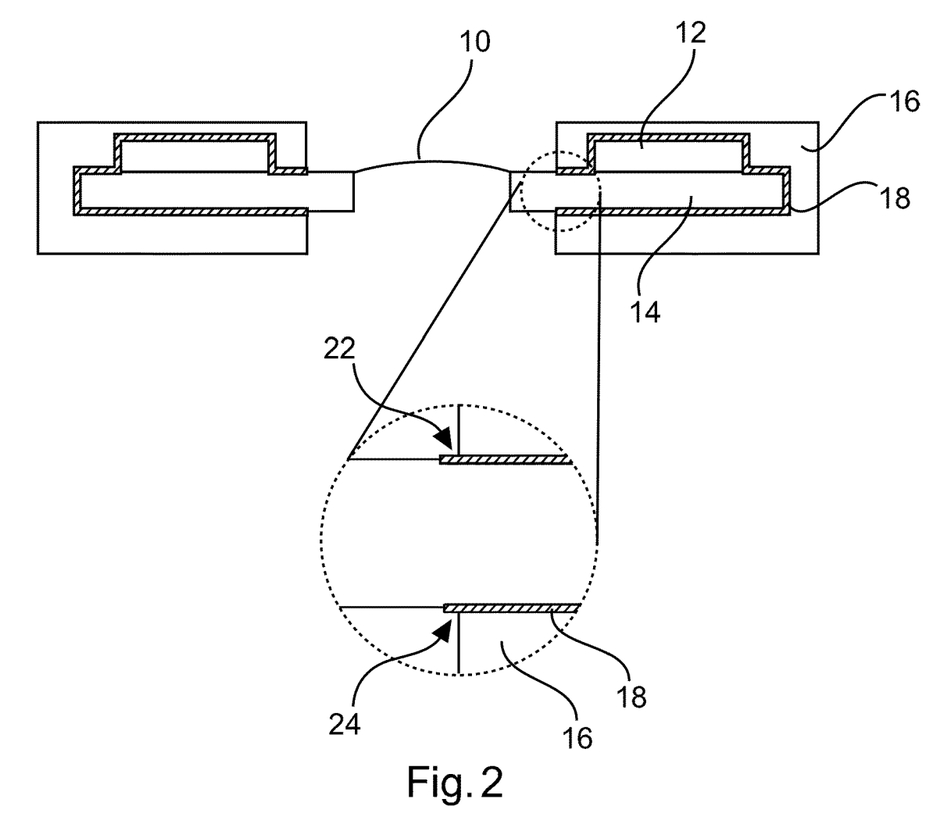
FIG. 2 shows an enlarged side-view of an aerosol generator as known in the prior art.

FIG. 2 illustrates the view of FIG. 1, with an enlarged area showing the relevant boundary areas. The boundary of the washer 14, adhesive layer 18, and boundary of the encapsulation element 16 is shown enlarged on a top side and a bottom side of the vibratory element. Water ingress due to boiling occurs via the path shown by arrows 22 and 24. The cause of the fluid ingress lies principally in the fact of the adhesion between the epoxy adhesive of the adhesive layer 18, and the (typically metal) surface of the washer 14. Metal granules of the washer 14 promote adhesion to the epoxy of the adhesive layer 18 via a mechanism of mechanical "locking-in" of adhesive around the metal granules, rather than by forming chemical bonds to the washer 14. This means that fluid may propagate through the spaces between the metal granules, advancing progressively with each boiling of the fluid. Eventually, the fluid will migrate as far as the piezoelectric element 12, and cause damage to it.

According to a first aspect of the invention, an aerosol generator for generating liquid droplets by nebulization is provided. The aerosol generator comprises:
- an aperture member comprising a plurality of apertures to provide the liquid droplets;
- a vibratory element arranged to generate a vibration of the aperture member; and
- an encapsulation element arranged to encapsulate a portion of the vibratory element.

An interface region is provided between the vibratory element and the encapsulation element, wherein the interface region comprises a sealing portion comprising a liquid resisting seal, provided as a first discontinuity formed on a face of the vibratory element and/or the encapsulation element.

Therefore, an aerosol generator is provided with improved resistance to fluid ingress. The first discontinuity formed on the face of the vibratory element acts as a barrier geometry, and functions to arrest the progress of the meniscus of an advancing fluid. In this way, the advancing fluid is stopped before it makes contact with the vibratory element. The first discontinuity causes an advancing liquid contact line to experience increased surface forces caused by the increase in surface area of the liquid contact line at the first discontinuity.

Figure 3:
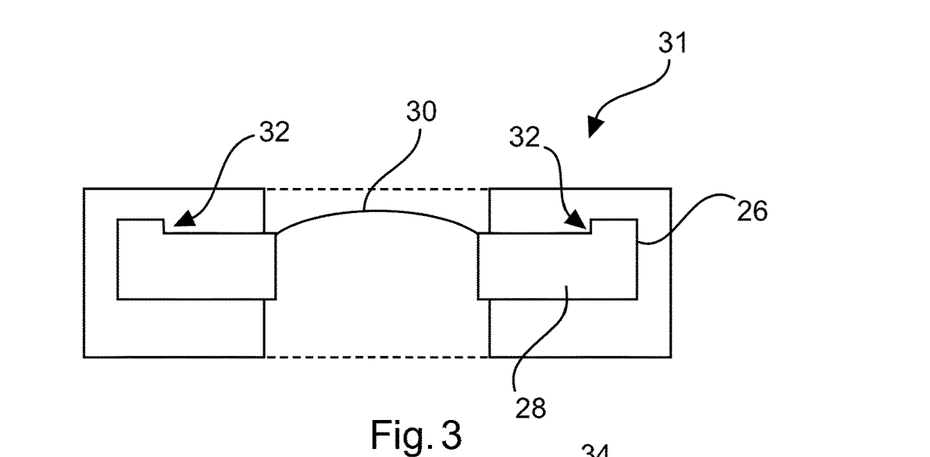
FIG. 3 shows a side-view of FIG. 3 shows an aerosol generator according to the first aspect.

FIG. 3 illustrates a side-view of a basic embodiment of an aerosol generator according to the first aspect. It will be appreciated that this view shows a side view of a cut-through of a "washer" type aerosol generator, although many other types and shapes of aerosol generator are relevant.

In FIG. 3, an encapsulation element 26 (typically an over moulded silicon rubber, or equivalent) encloses a vibratory element 28. A portion of the vibratory element 28 protrudes from the encapsulation element 26, and an aperture member 30 is attached to the protruding portion. In the illustration of FIG. 3, the interface region is considered to be any part of the vibratory element 28 which is in contact with the encapsulation element 26. The interface region may comprise an adhesive layer, as will be discussed subsequently. Alternatively, the interface region may be an "interference fit" in which the vibratory element 28 is attached to the encapsulation element 26 through the effects of a very tight contact. A first discontinuity 32 is provided in the surface of the vibratory element 28. The location where the first discontinuity is provided in the vibratory element is a sealing portion of the aerosol generator.

The first discontinuity may take many forms. The purpose of the first discontinuity is to provide a barrier geometry to impede, or stop, the propagation of fluid droplets along the interface region. It will be appreciated that the first discontinuity extends along a plane of the interface region to seal the entire interface region from water ingress.

In FIG. 3, the first discontinuity is provided as a single rectangular "step" feature extending along an annular path around the circumference of a top surface of the vibratory element 28. A fluid droplet propagating along the interface region will, upon reaching the first discontinuity 32, encounter a straight angle that interrupts the capillary forces pulling the fluid droplet along the interface region. Thus, the fluid droplet cannot propagate further along the interface region. Different forms, and specific details of the first discontinuity, will be provided subsequently.

Optionally, the aerosol generator is provided with an adhesive layer provided in the interface region.

Optionally, a portion of the vibratory element 28 is made from metal.

Optionally, a portion of the vibratory element 28 is a metal washer which holds a piezoelectric element.

Optionally, the interface region between the vibratory element 28 and the encapsulation element 26 encloses a flexible sealing member. The sealing member may comprise a pad of open-cell foam, or closed cell foam, for example. The presence of a discontinuity in the interface region stops the migration of fluid when a sealing member is present, because the flexible sealing member assumes the shape of the discontinuity when the vibratory element 28 and the interface element 26 are fixed together.

Figure 4A:
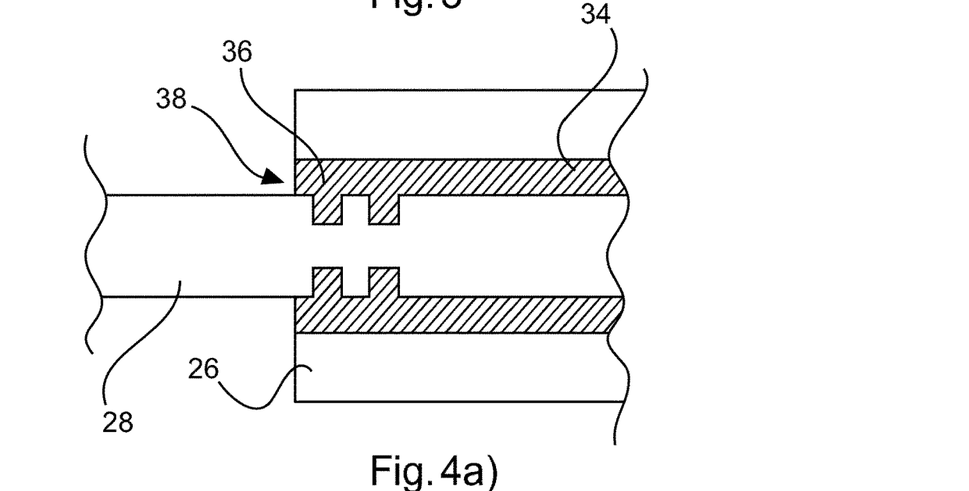
FIGS. 4a) and 4b) show side views of a portion of an aerosol generator according to embodiment, and a variant embodiment, of the first aspect.

FIG. 4a) shows a portion of an aerosol generator according to an embodiment of the first aspect. An adhesive layer 34 separates the encapsulation element 26 from the vibratory element 28 at the interface region. Part of the vibratory element 28 (such as the side of a washer) comprises a plurality of discontinuities 36 in a trench-like arrangement, although it will be appreciated that many types of discontinuity providing a barrier geometry to an advancing fluid may be provided, as will be discussed subsequently. The adhesive layer 34 fills in the gaps between the discontinuities in the interface region.

In the case that fluid ingress occurs mainly between the surface of the vibratory element 28 (such as a section of an annular metal washer holding a piezoelectric element) and the adhesive layer 34 (see arrow 38), the discontinuity 36 in the vibratory element 28 will prevent migration of the fluid droplet, owing to the barrier geometry presented by the discontinuity.

Figure 4B:
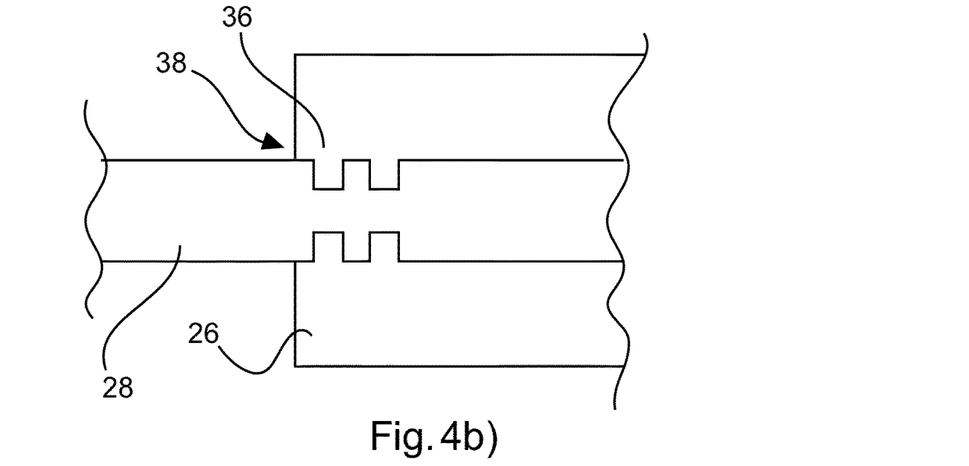

FIG. 4b) illustrates a variant embodiment of the first aspect in which the interface region is provided as an "interference fit". In other words, in the embodiment of FIG. 4b), the surface of the vibratory element 28 directly contact the encapsulation element 26 with no adhesive. A discontinuity is provided in the interface region. The discontinuity may be a step, a groove, or a wide range of discontinuities).

In the alternative, or additional, case that fluid ingress occurs between the encapsulation element and the adhesive layer, a discontinuity may be provided in the encapsulation element.

Figure 5A:
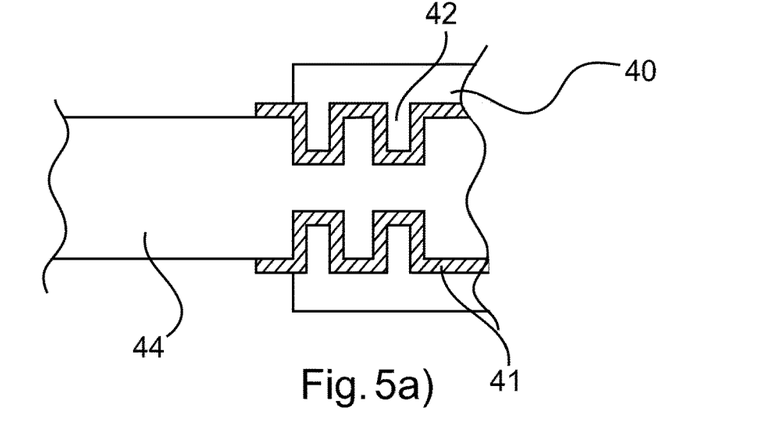
FIGS. 5a) and 5b) show side views of a portion of an aerosol generator according to an embodiment, and a variant embodiment, of the first aspect.
Figure 5B:
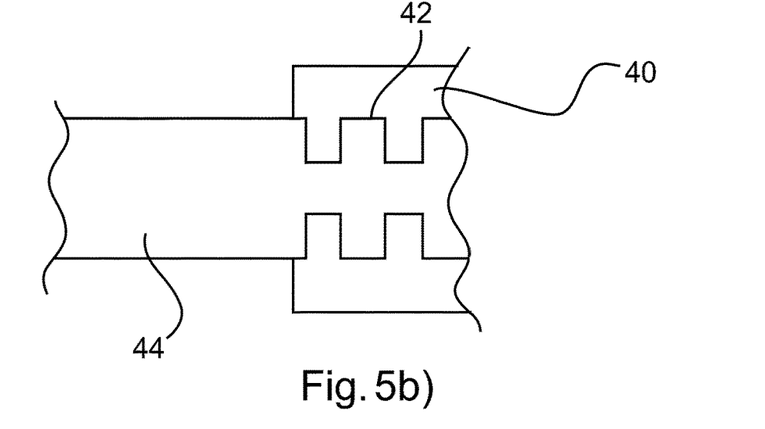

FIG. 5a) shows another fluid-ingress prevention arrangement for an aerosol generator. In this case, the encapsulation element 40 further comprises a second discontinuity 42 configured to form a complementary interlock structure with the first discontinuity of the vibratory element 44 at the sealing portion. In other words, the encapsulation element 40 is, itself provided with a discontinuity 42 which performs as a barrier geometry for fluid droplets propagating along the interface between the adhesive layer 41. The vibratory element 44 has a first discontinuity, as discussed above. Therefore, the structure illustrated in FIG. 5 can protect against fluid migration (i) between the vibratory element 44 and the adhesive layer 41, and (ii) between the adhesive layer 41 and the encapsulation element 40.

Figure 6:
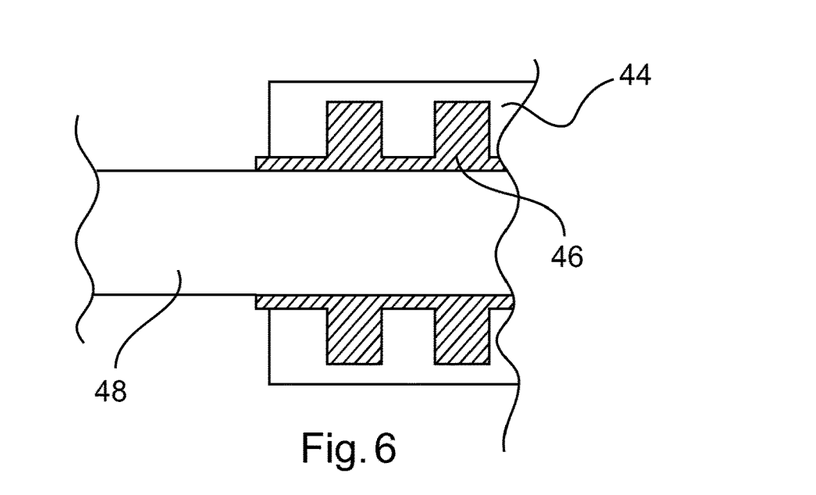
FIG. 6 shows a side view of a portion of an aerosol generator according to an embodiment of the first aspect.

FIG. 6 shows a variation of the fluid-ingress prevention arrangement for an aerosol generator. In this case, an encapsulation element 45 encapsulates a portion of a vibratory element 48. The vibratory element has no discontinuities. The encapsulation element 45 is provided with discontinuities in the interface region, into which the adhesive layer 46 is formed. Therefore, the variation of FIG. 6 is also applicable when fluid ingress occurs mainly between the adhesive layer 46 and the encapsulation element 45.

According to an embodiment of the first aspect, the vibratory element further comprises a piezo-electric element arranged in mechanical contact with an aperture member support structure. The aperture member support structure is configured to support the aperture member, and the interface region is provided on a portion of the aperture member support structure.

In other words, according to this embodiment, the vibratory element 28 is provided as a composite element.

Optionally, the vibratory element 28 is an annular member comprising an annular piezo element and an annular washer.

According to an embodiment of the first aspect, the vibratory element has a first side and a second side, and the sealing portion comprises a first sealing portion and a second sealing portion disposed on the first and the second sides of the vibratory element, respectively.

Accordingly, the vibratory element is protected from fluid ingress from two directions. For example, FIG. 4 illustrates a vibratory element having a first side and a second side. Because a first set of discontinuities is provided on the top side of the vibratory element, and a second set of discontinuities provided on the bottom side of the vibratory element, it is not possible for fluid to migrate under the bottom of the vibratory element 28.

According to an embodiment of the first aspect, the first discontinuity has a depth in the range of 1 to 500 microns, 10 to 500 microns, 10 to 100 microns, 10 to 80 microns, 10 to 60 microns, or preferably 10 to 50 microns.

According to an embodiment of the first aspect, the first discontinuity and/or second discontinuity is provided as a step discontinuity, having a depth in the range of 10 to 500 microns, 10 to 100 microns, 10 to 80 microns, 10 to 60 microns, or preferably 10 to 50 microns.

According to an embodiment of the first aspect, the first discontinuity and/or second discontinuity is provided as a groove, or a plurality of grooves.

According to an embodiment of the first aspect, the first discontinuity and/or second discontinuity is provided as a flat-bottomed trench, a pointed-trench, or an inverse trapezoidal shape trench.

It will be appreciated that the path of the discontinuity may take many different forms, to suit the form-factor of a particular aerosol generator. A washer-type aerosol generator has an annular shape, and therefore an annular discontinuity would be relevant in that case. However, many different paths for the continuity could be used (a "squiggle" pattern, for example) provided a complete seal around the area containing the piezo-electric element is provided.

Figure 7A:
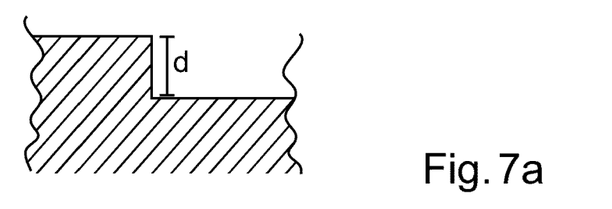
FIG. 7 shows side views of various embodiments of discontinuities, according to embodiments of the first aspect.
Figure 7B:
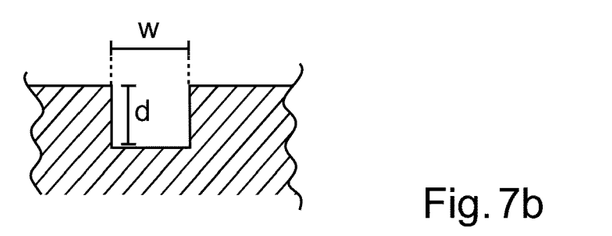
Figure 7C:
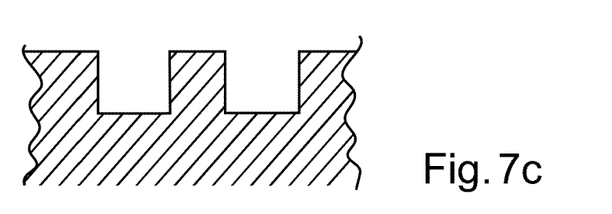
Figure 7D:
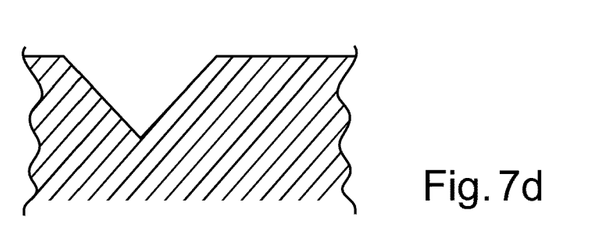
Figure 7E:
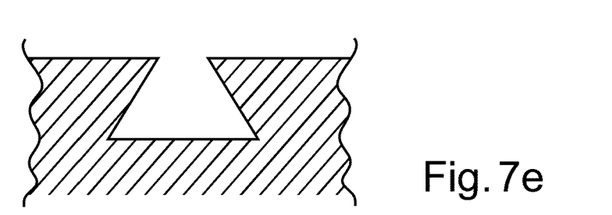

FIG. 7a) shows a discontinuity provided as a step discontinuity with a depth d, and a width w. FIG. 7b) shows a discontinuity in the form of a flat-bottomed trench, or two step-discontinuities facing each other. FIG. 7c) shows a plurality of flat-bottomed groove discontinuities. FIG. 7d) shows the discontinuity provided as a pointed-trench. FIG. 7e) shows the discontinuity provided as a inverse trapezoidal shape trench.

According to an embodiment of the first aspect, an aerosol generator is provided wherein the plurality of grooves is disposed on first and second opposite sides of the vibratory element, and the grooves of the first opposite side are offset in relation to the grooves of the second opposite side.

According to a second aspect of the invention, there is provided a nebulizer, comprising:
    an aerosol generator according to the first aspect, or its above-described embodiments.

Figure 8:
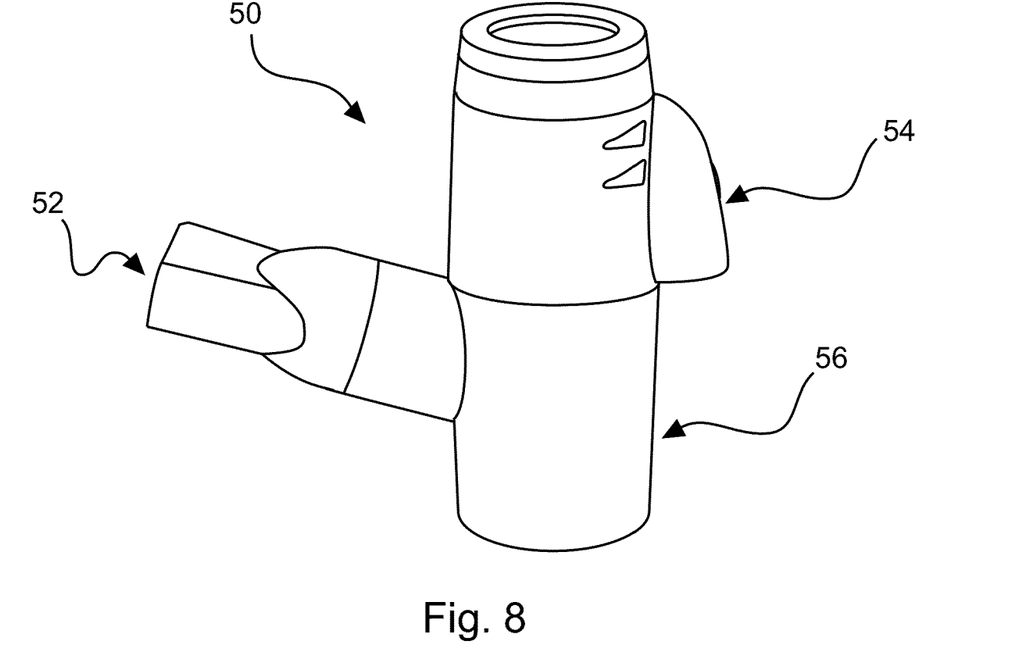
FIG. 8 shows a nebulizer according to the second aspect.

FIG. 8 illustrates a nebulizer according to the second aspect. The nebulizer comprises a lower section 56 which may be configured to hold an aerosol generator and/or a mixing chamber to enable generated aerosols to mix with an air stream. A mouthpiece 52 is in a fluid connection with the mixing chamber held in the lower section 56, enabling a generated aerosol to be entrained in an air stream generated by the inhalation of a patient. The upper section 54 of the nebulizer 50 may contain a fluid reservoir, and an aerosol generator for providing an aerosol to the mixing chamber. It will be appreciated that the preceding description refers to an exemplary nebulizer, but the aerosol generator according to the first aspect is suitable for use in a wide range of nebulizers.

According to a third aspect of the invention, there is provided a method of manufacturing an aerosol generator. The method comprises the steps of:

a) providing (60) a vibratory element arranged, in use of the component, to generate a vibration of an aperture member;

b) forming (62) a first discontinuity in a face of the vibratory element:

c) providing (64) an encapsulation element arranged to contact and encapsulate a portion of the vibratory element, to form an interface region incorporating a sealing portion with a liquid resisting seal provided by the first discontinuity.

Figure 9:
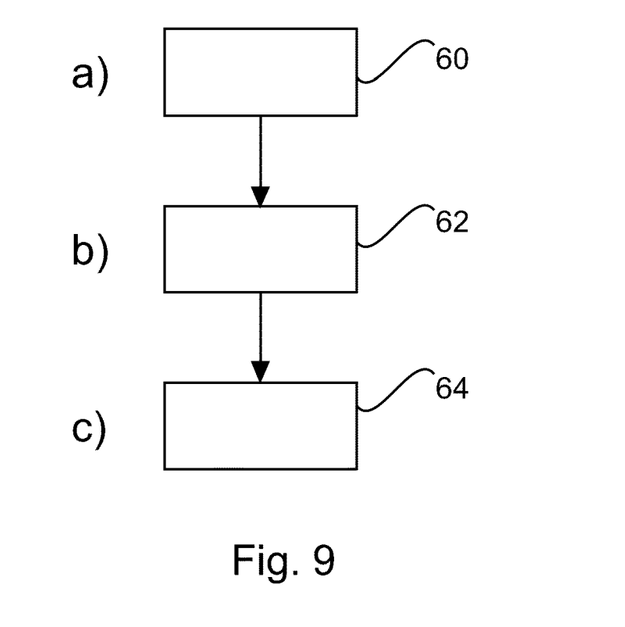
FIG. 9 shows a method of manufacturing an aerosol generator according to a third aspect.

FIG. 9 illustrates the method according to the third aspect.

According to an embodiment of the third aspect, the method further comprises the step b1):

b1) providing an adhesive on the interface region of a face of a vibratory element.

According to an embodiment of the third aspect, the method further comprises the step b2):

b2) providing on a face of the encapsulation element a complementary second discontinuity arranged to interlock with the first discontinuity of the vibratory element at the sealing portion.

According to an embodiment of the third aspect the first and/or second discontinuities are formed on the respective vibratory element or encapsulation element using a laser engraving technique.

It should to be noted that embodiments of the invention are described with reference to different subject-matters. In particular, some embodiments are described with reference to method-type claims, whereas other embodiments are described with reference to the device-type claims. However, a person skilled in the art will gather from the above, and the following description, that unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An aerosol generator for generating liquid droplets by nebulization, comprising:
   an aperture member comprising a plurality of apertures to provide the liquid droplets;
   a vibratory element comprising a piezo-electric element arranged to generate a vibration of the aperture member;
   an encapsulation arranged to encapsulate a portion of the vibratory element comprising the piezo-electric element; and
   an interface region arranged between the vibratory element and the encapsulation;
   wherein the interface region comprises a sealing portion, wherein the sealing portion comprises first and second substantially flat-bottomed discontinuities formed in at least one face of the vibratory element, wherein the first and second substantially flat-bottomed discontinuities have a depth in a range of 10 to 50 microns, wherein each of the first and second substantially flat-bottomed discontinuities comprise a plurality of grooves disposed on first and second opposite sides of the vibratory element, and wherein the grooves on the first opposite side are offset in relation to the grooves on the second opposite side.

2. The aerosol generator according to claim 1, further comprising: an adhesive layer provided in the interface region.

3. The aerosol generator according to claim 1,
   wherein the piezo-electric element is arranged in mechanical contact with an aperture member support structure;
   wherein the aperture member support structure is configured to support the aperture member; and
   wherein the interface region is provided on a portion of the aperture member support structure.

4. The aerosol generator according to claim 3, wherein the vibratory element has a first horizontal side and a second horizontal side, and the sealing portion comprises a first sealing portion and a second sealing portion disposed on the first and the second horizontal sides of the vibratory element, respectively.

5. The aerosol generator according to claim 1, wherein the groove, or grooves of the plurality of grooves, have an aspect ratio of 1.

6. The aerosol generator of claim 1, wherein the encapsulation further comprises a second discontinuity configured to form a complementary interlock structure with the first discontinuity of the vibratory element at the sealing portion.

7. A method of manufacturing an aerosol generator, comprising the steps of:
   a) providing a vibratory element comprising a piezo-electric element arranged, in use of the aerosol generator, to generate a vibration of an aperture member;
   b) forming first and second substantially flat-bottomed discontinuities having a depth in a range of 10 to 50 microns, each of the first and second substantially flat-bottomed discontinuities comprising a plurality of grooves disposed on first and second opposite sides of the vibratory element, wherein the grooves on the first opposite side are offset in relation to the grooves on the second opposite side; and
   c) providing an encapsulation arranged to encapsulate a portion of the vibratory element comprising the piezoelectric element, to form an interface region incorporating a sealing portion, and wherein the sealing portion comprises the first substantially flat-bottomed discontinuity of the first and second substantially flat-bottomed discontinuities.

8. The method of claim 7, further comprising providing an adhesive on the interface region.

9. The method of claim 7, further comprising providing on a face of the encapsulation a complementary second discontinuity arranged to interlock with the first discontinuity of the vibratory element at the sealing portion.

10. The method of claim 7, wherein the first discontinuity is formed on the vibratory element using a laser engraving technique.

11. The aerosol generator of claim 1, wherein the vibratory element comprises a first part and a second part and the interface region is arranged between the first part of the vibratory element in contact with a part of the encapsulation.

12. The aerosol generator of claim 11, wherein the second part of the vibratory element not in contact with the encapsulation is connected to the aperture member.

* * * * *